United States Patent
Sajiki et al.

(10) Patent No.: US 9,371,272 B2
(45) Date of Patent: Jun. 21, 2016

(54) METHOD FOR PRODUCING HYDROGEN OR HEAVY HYDROGENS, METHOD FOR PRODUCING HYDROGENATED (PROTIATED, DEUTERATED OR TRITIATED) ORGANIC COMPOUND, METHOD FOR HYDROGENATING (PROTIATING, DEUTERATING OR TRITIATING) ORGANIC COMPOUND, METHOD FOR DEHALOGENATING ORGANIC COMPOUND HAVING HALOGEN, AND BALL FOR USE IN MECHANOCHEMICAL REACTION

(71) Applicant: Shiono Chemical Co., Ltd., Tokyo (JP)

(72) Inventors: Hironao Sajiki, Gifu (JP); Yasunari Monguchi, Gifu (JP); Yoshinari Sawama, Gifu (JP); Shinichi Kondo, Aichi (JP); Yasushi Sasai, Gifu (JP)

(73) Assignee: Shiono Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/378,877

(22) PCT Filed: Feb. 8, 2013

(86) PCT No.: PCT/JP2013/053016
§ 371 (c)(1),
(2) Date: Aug. 14, 2014

(87) PCT Pub. No.: WO2013/121997
PCT Pub. Date: Aug. 22, 2013

(65) Prior Publication Data
US 2015/0025264 A1  Jan. 22, 2015

(30) Foreign Application Priority Data

Feb. 17, 2012 (JP) .................. 2012-032585

(51) Int. Cl.
| | | |
|---|---|---|
| C07C 221/00 | (2006.01) | |
| C07C 67/317 | (2006.01) | |
| C07C 213/02 | (2006.01) | |
| C07C 51/377 | (2006.01) | |
| C01B 3/02 | (2006.01) | |
| B01J 37/00 | (2006.01) | |
| C01B 3/04 | (2006.01) | |
| C01B 4/00 | (2006.01) | |
| C07C 5/05 | (2006.01) | |
| C07C 51/347 | (2006.01) | |
| C07C 69/78 | (2006.01) | |
| C07B 31/00 | (2006.01) | |
| C07C 5/08 | (2006.01) | |
| C07C 5/09 | (2006.01) | |
| B01J 23/06 | (2006.01) | |
| B01J 23/26 | (2006.01) | |
| B01J 23/755 | (2006.01) | |
| B01J 23/02 | (2006.01) | |
| B01J 23/42 | (2006.01) | |
| B01J 23/44 | (2006.01) | |
| B01J 23/46 | (2006.01) | |

(52) U.S. Cl.
CPC ............ *C07C 221/00* (2013.01); *B01J 37/0036* (2013.01); *C01B 3/02* (2013.01); *C01B 3/042* (2013.01); *C01B 4/00* (2013.01); *C07B 31/00* (2013.01); *C07C 5/05* (2013.01); *C07C 5/08* (2013.01); *C07C 5/09* (2013.01); *C07C 51/347* (2013.01); *C07C 51/377* (2013.01); *C07C 67/317* (2013.01); *C07C 69/78* (2013.01); *C07C 213/02* (2013.01); *B01J 23/02* (2013.01); *B01J 23/06* (2013.01); *B01J 23/26* (2013.01); *B01J 23/42* (2013.01); *B01J 23/44* (2013.01); *B01J 23/462* (2013.01); *B01J 23/464* (2013.01); *B01J 23/755* (2013.01); *C07B 2200/05* (2013.01); *C07C 2521/06* (2013.01); *C07C 2523/06* (2013.01); *C07C 2523/44* (2013.01); *Y02E 60/364* (2013.01); *Y02P 20/52* (2015.11)

(58) Field of Classification Search
None
See application file for complete search history.

(56) References Cited

U.S. PATENT DOCUMENTS

| | | |
|---|---|---|
| 8,871,980 B2 | 10/2014 | Sajiki et al. |
| 2004/0208820 A1 | 10/2004 | Watanabe et al. |
| 2010/0243469 A1 | 9/2010 | Skomsvold |

FOREIGN PATENT DOCUMENTS

| | | |
|---|---|---|
| JP | 2001 47026 | 2/2001 |
| JP | 2001-517641 | 10/2001 |

(Continued)

OTHER PUBLICATIONS

Description of JP-2007-031169—Machine translation date: 2007.*

(Continued)

*Primary Examiner* — Yevegeny Valenrod
(74) *Attorney, Agent, or Firm* — Oblon, McClelland, Maier & Neustadt, L.L.P

(57) ABSTRACT

Objects are to provide efficient methods for producing hydrogen or heavy hydrogens and for hydrogenating (protiating, deuterating or tritiating) an organic compound, and to provide an equipment and the like used therefor. A method for producing hydrogen or heavy hydrogens, containing subjecting water or heavy water to mechanochemical reaction in the presence of a catalyst metal, in which an energy density of a rotational acceleration of 75 G or more is applied to water or heavy water for 25 minutes or more, a method for producing a hydrogenated (protiated, deuterated or tritiated) organic compound, a method for hydrogenating (protiating, deuterating or tritiating) an organic compound, a method for dehalogenating an organic compound having halogen, and a ball for mechanochemical reaction are provided.

2 Claims, No Drawings

(56) References Cited

FOREIGN PATENT DOCUMENTS

| | | |
|---|---|---|
| JP | 2004 123517 | 4/2004 |
| JP | 2005-248027 | 9/2005 |
| JP | 2007 31169 | 2/2007 |
| JP | 2008 273758 | 11/2008 |
| JP | 2010 120825 | 6/2010 |
| WO | WO 2005/053854 | 6/2005 |
| WO | 2012 023546 | 2/2012 |

OTHER PUBLICATIONS

International Search Report Issued Apr. 16, 2013 in PCT/JP13/053016 Filed Feb. 8, 2013.

Combine Office Action and Search Report issued Jun. 25, 2015 in Chinese Patent Application No. 201380009787.1 (with English translation of category of cited documents).

Extended Search Report issued Mar. 18, 2016, in European patent application No. 13 748 505.8.

* cited by examiner

METHOD FOR PRODUCING HYDROGEN OR HEAVY HYDROGENS, METHOD FOR PRODUCING HYDROGENATED (PROTIATED, DEUTERATED OR TRITIATED) ORGANIC COMPOUND, METHOD FOR HYDROGENATING (PROTIATING, DEUTERATING OR TRITIATING) ORGANIC COMPOUND, METHOD FOR DEHALOGENATING ORGANIC COMPOUND HAVING HALOGEN, AND BALL FOR USE IN MECHANOCHEMICAL REACTION

TECHNICAL FIELD

The present invention relates to an effective method for producing hydrogen or heavy hydrogens (deuterium and tritium) utilizing mechanochemical reaction, a method for producing a hydrogenated (protiated, deuterated or tritiated) organic compound, a method for hydrogenating (protiating, deuterating or tritiating) an organic compound, a method for dehalogenating an organic compound having halogen, and a ball for use in mechanochemical reaction.

BACKGROUND ART

Hydrogen has been utilized in various fields in industry. For example, hydrogen has been used as a raw material for production of ammonia by the Harber-Bosch process, production of hydrochloric acid by photoreaction of chlorine gas, modification of fat and oil, such as corn oil and cottonseed oil, by adding thereto for hardening (solidification), and the like; a reducing agent for reduction of a metallic mineral (oxide), production of aniline through reduction of nitrobenzene, catalytic reduction of benzene in production of nylon 66, synthesis of methyl alcohol through reduction of carbon monoxide, desulfurization and the like; and the like.

Furthermore, hydrogen forms no emission other than water on combustion, for example, does not form particulate matters and an exhaust gas including carbon dioxide, and thus is expected as alternate energy, and hydrogen is used as a fuel for internal combustion in a hydrogen vehicle with hydrogen-fueled engine, and is also used as a fuel for a rocket and a fuel cell.

Hydrogen is industrially mass-produced as a by-product of steam reforming and partial oxidation of hydrocarbons (hydrocarbon gas reforming process). In this process, methane gas in natural gas, a paraffin compound, ethylene, propylene or the like is reacted with steam under high temperature with nickel as a catalyst to form hydrogen and carbon monoxide, and by-produced carbon monoxide is further reacted with steam to form carbon dioxide and hydrogen gas. As an alternative method, hydrogen that is formed as a by-product of electrolysis of seawater in the soda industry and the salt production industry may also be utilized.

Hydrogenation reaction where an organic compound is reacted with hydrogen is widely used in organic synthetic chemistry, and many useful compounds are formed by the process. The hydrogenation reaction includes various methods, such as reaction utilizing an alkali metal or the like, reaction utilizing a metal hydride or a metal hydride complex, reaction utilizing diborane or hydrazine, and a reaction utilizing catalytic hydrogenation.

However, the industrial methods for production of hydrogen described above require a large-scale equipment and may not be utilized for convenient production of hydrogen. There is an experimental method of utilizing hydrogen formed by dissolving a metal in a diluted acid or an alcohol, but the problem is that a metal is irreversibly dissolved, and the solution having the metal dissolved therein is necessarily treated.

In the hydrogenation reaction described above, the methods utilizing an alkali metal, a metal hydride, a metal hydride complex, diborane, hydrazine or the like have problems of high cost and hazardous nature of the reaction reagents used, and the method utilizing catalytic hydrogenation is also disadvantageous in that a special metal catalyst is necessarily used.

SUMMARY OF INVENTION

Technical Problem

As a result of various experiments made by the present inventors in view of the aforementioned current condition, the inventors have found a method for conveniently providing hydrogen or heavy hydrogens, and the like by utilizing mechanochemical reaction and have filed an application for patent (PCT/JP2011/68535, international filing date: Aug. 16, 2011, priority date: Aug. 18, 2010). On the basis of a detailed study of the method, the present invention aims to provide methods for efficiently providing hydrogen or heavy hydrogens and hydrogenating (protiating, deuterating or tritiating) an organic compound, an equipment used therefor, and the like.

Solution to Problem

As a result of earnest investigations for solving the problem, the inventors have found that hydrogen or heavy hydrogens may be obtained efficiently by applying a particular amount or more of energy to water or heavy water. The inventors have also found that hydrogen or heavy hydrogens may be obtained efficiently, and an organic compound may be hydrogenated (protiated, deuterated or tritiated), by using a ball having a particular structure in mechanochemical reaction. The inventors have further found that hydrogen or heavy hydrogens may be obtained efficiently, and an organic compound may be hydrogenated (protiated, deuterated or tritiated), by using a particular catalyst metal in mechanochemical reaction. Thus, the present invention has been completed.

The present invention includes the following items (1) to (10).

(1) A method for producing hydrogen or heavy hydrogens, containing subjecting water or heavy water to mechanochemical reaction in the presence of a catalyst metal, an energy density of a rotational acceleration of 75 G or more being applied to water or heavy water for 25 minutes or more.

(2) A ball for mechanochemical reaction, containing a catalyst metal on at least a part of a surface of the ball.

(3) A method for producing hydrogen or heavy hydrogens, containing subjecting water or heavy water to mechanochemical reaction by using the ball for mechanochemical reaction according to the item (2).

(4) A method for producing a hydrogenated (protiated, deuterated or tritiated) organic compound, containing subjecting an organic compound and water or heavy water to mechanochemical reaction by using the ball for mechanochemical reaction according to the item (2).

(5) A method for hydrogenating (protiating, deuterating or tritiating) an organic compound, containing subjecting an organic compound and water or heavy water to mechanochemical reaction by using the ball for mechanochemical reaction according to the item (2).

(6) A method for dehalogenating an organic compound having halogen, containing subjecting an organic compound having halogen and water or heavy water to mechanochemical reaction by using the ball for mechanochemical reaction according to the item (2).

(7) A method for producing hydrogen or heavy hydrogens, containing subjecting water or heavy water to mechanochemical reaction by using a ball for mechanochemical reaction that is essentially free of catalyst metal, and one or more kinds selected from a transition metal selected from palladium, chromium, nickel, zinc, aluminum, magnesium, platinum, ruthenium and rhodium, and an oxide of the transition metal.

(8) A method for producing a hydrogenated (protiated, deuterated or tritiated) organic compound, containing subjecting an organic compound and water or heavy water to mechanochemical reaction by using a ball for mechanochemical reaction that is essentially free of catalyst metal, and one or more kinds selected from a transition metal selected from palladium, chromium, nickel, zinc, aluminum, magnesium, platinum, ruthenium and rhodium, and an oxide of the transition metal.

(9) A method for hydrogenating (protiating, deuterating or tritiating) an organic compound, containing subjecting an organic compound and water or heavy water to mechanochemical reaction by using a ball for mechanochemical reaction that is essentially free of catalyst metal, and one or more kinds selected from a transition metal selected from palladium, chromium, nickel, zinc, aluminum, magnesium, platinum, ruthenium and rhodium, and an oxide of the transition metal.

(10) A method for dehalogenating an organic compound having halogen, containing subjecting an organic compound having halogen and water or heavy water to mechanochemical reaction by using a ball for mechanochemical reaction that is essentially free of catalyst metal, and one or more kinds selected from a transition metal selected from palladium, chromium, nickel, zinc, aluminum, magnesium, platinum, ruthenium and rhodium, and an oxide of the transition metal.

ADVANTAGEOUS EFFECTS OF INVENTION

The method for producing hydrogen or heavy hydrogens according to the item (1) of the invention may have a high conversion rate of water or heavy water to hydrogen or heavy hydrogens and thus may provide hydrogen or heavy hydrogens efficiently.

The ball for mechanochemical reaction according to the item (2) of the invention may allow mechanochemical reaction to proceed efficiently and may be reused repeatedly.

The method for producing hydrogen or heavy hydrogens according to the item (3) of the invention, the method for producing a hydrogenated (protiated, deuterated or tritiated) organic compound according to the item (4) and the method for hydrogenating (protiating, deuterating or tritiating) an organic compound according to the item (5) may provide hydrogen or heavy hydrogens, or a hydrogenated (protiated, deuterated or tritiated) organic compound efficiently and repeatedly due to the use of the ball for mechanochemical reaction according to the item (2) of the invention.

The method for dehalogenating an organic compound having halogen according to the item (6) of the invention may dehalogenate an organic compound having halogen efficiently and repeatedly due to the use of the ball for mechanochemical reaction according to the item (2) of the invention.

The method for producing hydrogen or heavy hydrogens according to the item (7) of the invention, the method for producing a hydrogenated (protiated, deuterated or tritiated) organic compound according to the item (8) and the method for hydrogenating (protiating, deuterating or tritiating) an organic compound according to the item (9) may facilitate control of the reaction of forming hydrogen or heavy hydrogens, or a hydrogenated (protiated, deuterated or tritiated) organic compound since the ball used in the mechanochemical reaction and the catalyst are separately provided, and furthermore may complete the reaction within a short period of time even under a low rotation number since the number of contacts of water, heavy water or an organic compound with a catalyst metal may be increased.

The method for dehalogenating an organic compound having halogen according to the item (10) of the invention may facilitate control of the reaction of forming a dehalogenated organic compound since the ball used in the mechanochemical reaction and the catalyst are separately provided, and furthermore may complete the reaction within a short period of time even under a low rotation number since the number of contacts of water, heavy water or an organic compound having halogen with a catalyst metal may be increased.

DESCRIPTION OF EMBODIMENTS

The term "heavy water" in the present invention means water that is formed of $^2$H (D) or $^3$H (T), which is an isotope of hydrogen ($^1$H), $^{17}$O or $^{18}$O, which is an isotope of oxygen ($^{16}$O), or a combination thereof, and specific examples thereof include $D_2O$ and $T_2O$. The term "heavy hydrogen" herein means hydrogen that is formed of an isotope of hydrogen, and specific examples thereof include $D_2$ and $T_2$. The term "deuteration or tritiation" herein means partial or total replacement of hydrogen in ordinary hydrogenation by D or T.

The item (1) of the invention is a method for producing hydrogen or heavy hydrogens, containing subjecting water or heavy water to mechanochemical reaction in the presence of a catalyst metal, in which an energy density of a rotational acceleration of 75 G or more is applied to water or heavy water for 25 minutes or more.

The mechanochemical reaction in this method is performed by enhancing the activity of a reactant with mechanical energy, such as impact and friction. Examples of a mechanochemical equipment that may be used in the item (1) of the invention include one that has a reaction vessel and an agitation medium imparting mechanical energy and applies mechanical energy by rotation to water or heavy water in the reaction vessel, and specific examples thereof include a planetary ball mill, a ball mill and a mixer mill. Among these, a planetary ball mill, in which a reaction vessel and an agitation medium are concurrently rotated, is preferably used from the standpoint of the agitation efficiency and the energy to be imparted.

The planetary ball mill equipment is an equipment having a function of homogeneously mixing and finely pulverizing powder of a metal or a ceramic, and is composed of a planetary ball mill reaction vessel and an atmosphere controlled chamber. Powder of a metal or a ceramic (i.e., a material to be pulverized) and a ball as an agitation medium are placed in the ball mill reaction vessel, which is set in the equipment, and the ball mill reaction vessel undergoes a revolutionary motion like a motion of a planet while undergoing a rotational motion inside the atmosphere controlled chamber, thereby mixing and pulverizing the powder efficiently in a short period of time. Furthermore, the atmosphere in the entire planetary ball mill is controlled, and thus it is possible to mix and pulverize a powder prone to be deteriorated in the air.

Examples of the reaction vessel and the ball as an agitation medium used in the planetary ball mill equipment include those formed of such materials as stainless steel, agate, alumina, tungsten carbide, chrome steel, zirconia, silicon nitride, brass and Teflon (a registered trade name). Among these materials, stainless steel, which is an alloy of iron and chromium, nickel and the like, is preferred. The size of the vessel used in the planetary ball mill equipment is not particularly limited, and may be approximately from 1 to 1,000 $cm^3$. The size of the ball is also not particularly limited, and the diameter thereof may be approximately from 2 to 20 mm. Particularly preferred examples of the planetary ball mill include Planetary Ball Mill Quartet P-7 (produced by Fritsch GmbH, Germany), Planetary Ball Mill Premium Line-7 (produced by Fritsch GmbH, Germany) and Planetary Ball Mill PM-100 (produced by Retsch GmbH & Co., Germany).

In the item (1) of the invention, for performing mechanochemical reaction in the presence of a catalyst metal, it is only necessary to add the catalyst metal to the mechanochemical reaction system in an amount sufficient to exhibit the catalytic action, for example, more than 0.001% by mole with respect to water. Examples of the catalyst metal include transition metals, such as palladium, iron, nickel, chromium, magnesium and zinc, and oxides of the transition metals, and preferred examples thereof include iron, iron(II) hydroxide, nickel, nickel(II) oxide, chromium, chromium(III) oxide and palladium. The catalyst metals may be used solely or as a combination of two or more kinds thereof. The catalyst metal may be added to the reaction vessel used for the mechanochemical reaction in the form of powder, wire, foil or the like, may be contained in the reaction vessel or the agitation medium, such as the ball and the agitation bar, used for the mechanochemical reaction, or may be provided on the agitation medium by plating or the like.

The mechanochemical reaction condition in the item (1) of the invention is an application of an energy density of a rotational acceleration of 75 G or more, and preferably 83 G or more, to water or heavy water for 25 minutes or more, and preferably 30 minutes or more. Under the condition, the conversion rate of water or heavy water to hydrogen or heavy hydrogens may be 60% or more, and preferably 70% or more.

For practicing the method for producing hydrogen or heavy hydrogens of the item (1) of the invention, water or heavy water may be placed in the reaction vessel of the above-described equipment capable of performing the mechanochemical reaction, and the agitation medium may be driven in the presence of the catalyst metal, preferably one or more kinds selected from iron, iron(II) hydroxide, chromium, chromium(III) oxide, nickel, magnesium and zinc, to apply the energy of the aforementioned condition to water or heavy water in the reaction vessel for performing the mechanochemical reaction, thereby generating hydrogen or heavy hydrogens. Hydrogen or heavy hydrogens thus generated in the reaction vessel may be collected by an ordinary method.

The item (1) of the invention will be described specifically in the case of performing with a planetary ball mill (Planetary Ball Mill Premium Line-7 produced by Fritsch GmbH, Germany). Water or heavy water may be placed in the reaction vessel of the equipment in an amount of approximately from 0.1 to 20% by mass (which may be hereinafter referred simply to as "%") of the capacity of the vessel, in which approximately from 1 to 100 pieces of the agitation medium (ball) may be placed and the catalyst metal in an amount of approximately from 0.01 to 100% by mole with respect to water or heavy water may also be placed as needed in addition to the catalyst metal contained in the reaction vessel or the agitation medium, and the equipment may be rotated at approximately 1,050 rpm or more, and preferably 1,100 rpm or more, for agitating for approximately 25 minutes or more, and preferably 30 minutes or more.

The item (2) of the invention is a ball for mechanochemical reaction, containing a catalyst metal on at least apart of a surface of the ball. The use of the ball accelerates the reaction by the catalyst metal to perform mechanochemical reaction efficiently, thereby reducing the reaction time.

The ball may be an agitation medium in mechanochemical reaction, and the size of the ball, which is not particularly limited, may be appropriately determined depending on the size of the reaction vessel and is preferably approximately from 2 to 20 mm in diameter. Examples of the material for the ball include stainless steel, agate, alumina, tungsten carbide, chrome steel, zirconia, silicon nitride, brass and Teflon (a registered trade name). Among these materials, stainless steel, which is an alloy of iron and chromium, nickel and the like, is preferred.

Examples of the catalyst metal include one or more kinds of transition elements. Specifically, in the case where the catalyst metal is used in producing hydrogen or heavy hydrogens from water or heavy water, examples thereof include transition metals, such as palladium, chromium, nickel, zinc, aluminum, magnesium, platinum, ruthenium and rhodium, and oxides of the transition metals, and preferred examples thereof include nickel, nickel(II) oxide, chromium, chromium(III) oxide, magnesium and zinc. In the case where the catalyst metal is used in hydrogenating (protiating, deuterating or tritiating) an organic compound with water or heavy water, examples thereof include a transition metal, preferably nickel, nickel(II) oxide, chromium, chromium(III) oxide and palladium.

For providing the catalyst metal on at least a part of a surface of the ball, examples of the method therefor include a method of making a hole on the surface of the ball with a drill or the like and embedding wire or the like of the catalyst metal therein, a method of immersing the ball in a solution of a salt of the catalyst metal and drying to attach the catalyst metal to the surface of the ball, a method of agitating powder of the catalyst metal and the ball with a planetary ball mill equipment to attach the catalyst metal to the surface of the ball, and a method of depositing the catalyst metal to the surface of the ball by plating or sputtering. Among these methods, the method of making a hole on the surface of the ball with a drill or the like and embedding wire or the like of the catalyst metal therein is preferred since the method facilitates reuse of the ball. The hole for embedding the catalyst metal may have a diameter of approximately 1 mm and a depth of approximately 1 mm, and at least one hole may be provided.

The ball for mechanochemical reaction of the item (2) of the invention (which is hereinafter referred to as "a ball A") described above may be used for mechanochemical reaction.

The mechanochemical reaction is performed by enhancing the activity of a reactant with mechanical energy, such as impact and friction. Examples of a mechanochemical equipment that can use the ball A of the item (2) of the invention include one that has a reaction vessel and a ball as an agitation medium imparting mechanical energy, and specific examples thereof include a planetary ball mill and a ball mill. Among these, a planetary ball mill, in which a reaction vessel and an agitation medium are concurrently rotated, is preferably used from the standpoint of the agitation efficiency and the energy to be imparted.

The planetary ball mill equipment is an equipment having a function of homogeneously mixing and finely pulverizing powder of a metal or a ceramic, and is composed of a planetary ball mill reaction vessel and an atmosphere controlled chamber. Powder of a metal or a ceramic (i.e., a material to be pulverized) and the ball A as an agitation medium are placed in the ball mill reaction vessel, which is set in the equipment, and the ball mill reaction vessel undergoes a revolutionary motion like a motion of a planet while undergoing a rotational motion inside the atmosphere controlled chamber, thereby mixing and pulverizing the powder efficiently in a short period of time. Furthermore, the atmosphere in the entire planetary ball mill is controlled, and thus it is possible to mix and pulverize a powder prone to be deteriorated in the air.

Examples of the reaction vessel used in the planetary ball mill equipment include those formed of such materials as stainless steel, agate, alumina, tungsten carbide, chrome steel, zirconia and silicon nitride. Among these materials, stainless steel, which is an alloy of iron and chromium, nickel and the like, is preferred. The size of the vessel used in the planetary ball mill equipment is not particularly limited, and may be approximately from 1 to 1,000 cm$^3$. Particularly preferred examples of the planetary ball mill include Planetary Ball Mill Quartet P-7 (produced by Fritsch GmbH, Germany), Planetary Ball Mill Premium Line-7 (produced by Fritsch GmbH, Germany) and Planetary Ball Mill PM-100 (produced by Retsch GmbH & Co., Germany).

The ball A is especially suitable for use in a method for producing hydrogen or heavy hydrogens, a method for producing a hydrogenated (protiated, deuterated or tritiated) organic compound, a method for dehalogenating an organic compound having halogen, by utilizing mechanochemical reaction. These methods will be described below.

For practicing the method for producing hydrogen or heavy hydrogens by using the ball A (the item (3) of the invention), water or heavy water may be subjected to mechanochemical reaction by using the ball A. Specifically, the ball A and water or heavy water may be placed in the reaction vessel of the above-described equipment capable of performing the mechanochemical reaction, and the equipment may be driven to perform the mechanochemical reaction, thereby generating hydrogen or heavy hydrogens. Hydrogen or heavy hydrogens thus generated in the reaction vessel may be finally collected by an ordinary method.

The case where the item (3) of the invention is performed with a planetary ball mill will be specifically described. Water or heavy water may be placed in the reaction vessel of the planetary ball mill equipment in an amount of approximately from 0.1 to 20% by mass (which may be hereinafter referred simply to as "%") of the capacity of the vessel, in which approximately from 1 to 100 pieces of the ball A solely or in total of the ball and a ball for mechanochemical reaction ordinarily used may be placed and the catalyst metal may be added as needed, and the equipment may be rotated for approximately from 0.1 to 12 hours, and preferably approximately from 0.5 to 6 hours, at approximately from 400 to 1,200 rpm, and preferably from 800 to 1,100 rpm, for performing agitation. On agitation, the rotation direction may be preferably reversed as appropriate, and in the case where the agitation is performed continuously, a rest period is preferably provided. The conversion rate of water or heavy water to hydrogen or heavy hydrogens in the first embodiment of the invention may be approximately from 20 to 100% depending on the equipment used, the reaction conditions and the like.

For practicing the method for producing a hydrogenated (protiated, deuterated or tritiated) organic compound by using the ball A (the item (4) of the invention), an organic compound and water or heavy water may be subjected to mechanochemical reaction by using the ball A. Specifically, the ball A, an organic compound and water or heavy water may be placed in the reaction vessel of the above-described equipment capable of performing the mechanochemical reaction, and the equipment may be driven to perform the mechanochemical reaction, thereby hydrogenating (protiating, deuterating or tritiating) the organic compound. The hydrogenation (protiation, deuteration or tritiation) of the organic compound may be confirmed by a conventional method, such as $^1$H NMR and GC/MS.

The organic compound used in the item (4) of the invention is not particularly limited as long as the organic compound is capable of being hydrogenated (protiated, deuterated or tritiated), and examples thereof include organic compounds that have an unsaturated bond, such as a double bond and a triple bond, a substituent having a high oxidation degree, such as an aldehyde group, a ketone group, a nitro group and an azido group, and halogen, in the skeleton thereof.

Water or heavy water added along with an organic compound in the item (4) of the invention introduces hydrogen or heavy hydrogens, and thus the degree of hydrogenation (protiation, deuteration or tritiation) may be controlled by the amount of thereof added. In order to increase the degree of hydrogenation (protiation, deuteration or tritiation), a larger amount of water or heavy water may be added, and in the case where only a low degree of hydrogenation (protiation, deuteration or tritiation) may be provided, the amount of water or heavy water added may be rather small. The amount of water or heavy water added is greatly influenced by the ease of hydrogenation (protiation, deuteration or tritiation) of the organic compound, and thus may be experimentally determined before practice. In the item (4) of the invention, furthermore, the degree of hydrogenation (protiation, deuteration or tritiation) of the organic compound may also be controlled by controlling the mechanical energy, such as impact and friction, in the mechanochemical reaction. In order to increase the degree of hydrogenation (protiation, deuteration or tritiation), a larger size of the ball A may be used and the number of the pieces of the ball A or the rotation speed may increased, and in the case where only a low degree of hydrogenation (protiation, deuteration or tritiation) may be provided, a smaller size of the ball A may be used and the number of the pieces of the ball A or the rotation speed may be decreased.

On performing the item (4) of the invention as described above, water or heavy water in the reaction vessel is converted to hydrogen or heavy hydrogens, with which the organic compound is hydrogenated (protiated, deuterated or tritiated). The conversion rate of the organic compound to the hydrogenated (protiated, deuterated or tritiated) organic compound in the item (4) of the invention may be approximately from 70 to 100% depending on the equipment used, the reaction conditions and the like.

According to the item (4) of the invention, an unsaturated bond (such as a double bond and a triple bond) in a skeleton of an organic compound may be converted to a saturated bond, and furthermore, a substituent having a high oxidation degree (such as an aldehyde group, a ketone group and a nitro group) may be converted to a substituent having a low oxidation degree (such as a hydroxyalkyl group, a hydroxy group and an amino group), and halogen in a halide compound may be removed to form a dehalogenated compound.

Specifically, compounds having the following basic skeletons may be converted to corresponding reduced compounds through hydrogenation (protiation, deuteration or tritiation). Compounds capable of being hydrogenated (protiated, deuterated or tritiated) are also shown below, but the compounds capable of being hydrogenated (protiated, deuterated or tritiated) in the item (4) of the invention are not limited thereto. In the compounds, a methyl group is shown as a representative of an alkyl group (i.e., a functionalized aliphatic chain), and benzene or phenyl is shown as a representative of an aryl group (i.e., a functionalized aromatic ring including benzene, furan, pyrrole, thiophene and the like).

<Triple Bond-Containing Compound>
Terminal alkyne body: methylacetylene, ethynylbenzene
Disubstituted alkyne body: diphenylacetylene, dimethylacetylene, methylphenyl acetylene
<Double Bond-Containing Compound>
Monosubstituted alkene body: phenylethylene, methylethylene
Disubstituted alkene body: (E)-1,2-diphenylethylene, (Z)-1,2-diphenylethylene, (E)-1,2-dimethylethylene, (Z)-1,2-dimethylethylene, 1,1-diphenylethylene, 1,1-dimethylethylene, 1-methyl-1-phenylethylene, (E)-1-methyl-2-phenylethylene, (Z)-1-methyl-2-phenylethylene
Trisubstituted alkene body: 1,1,2-triphenylethylene, 1,1,2-trimethylethylene, 1,1-diphenyl-2-methylethylene, 1-phenyl-1,2-dimethylethylene
Tetrasubstituted alkene body: 1,1,2,2,-tetraphenylethylene, 1,1,2,2,-tetramethylethylene, 1,1,2-triphenyl-2-methylethylene, 1,1-diphenyl-2,2-dimethylethylene, 1-phenyl-1,2,2-trimethylethylene, (E)-1,2-diphenyl-1,2-dimethylethylene, (Z)-1,2-diphenyl-1,2-dimethylethylene
Aromatic ring: benzene, biphenyl, pyridine, furan, pyrrole, thiophene, naphthalene, quinoline, anthracene, imidazole, indole, benzofuran, oxazole
<Carbonyl Group-Containing Compound*>
Aldehyde body: methyl aldehyde, phenylaldehyde
Ketone body: dimethyl ketone, diphenyl ketone, methyl phenyl ketone
Imine body: N-methyl-methylimine, N-phenyl-methylimine, N-methyl-dimethylimine, N-methyl-diphenylimine, N-methyl-methylphenylimine, N-phenyl-dimethylimine, N-phenyl-diphenylimine, N-phenyl-methylphenylimine
Oxime: N-hydroxy-methylimine, N-hydroxy-dimethylimine, N-hydroxy-diphenylimine, N-hydroxy-methylphenylimine
*: It includes a compound having a carbonyl group, the oxygen atom of which is substituted by the other atom or group.
<Nitro Group-Containing Compound>
Nitro body: nitromethane, nitrobenzene
<Azido Group-Containing Compound>
Azide body: methane azide, benzene azide
<Halogen-Containing Compound>
Fluorine body: methyl fluoride, fluorobenzene
Chlorine body: methyl chloride, chlorobenzene
Bromine body: methyl bromide, bromobenzene
Iodine body: methyl iodide, iodobenzene
<Benzyl Ether Group-Containing Compound>
Benzyl ether body: phenyl methyloxymethane, phenyl methyloxybenzene Particularly preferred specific examples of the compound to be hydrogenated (protiated, deuterated or tritiated) in the item (4) of the invention and the reduced compound thereof are shown below.

| Compound to be hydrogenated (protiated, deuterated or tritiated) | Reduced compound |
| --- | --- |
| ethynylbenzene | ethylbenzene |
| diphenylacetylene | 1,2-diphenylethane |
| phenylethylene | ethylbenzene |
| (E)-1,2-diphenylethylene | 1,2-diphenylethane |

-continued

| Compound to be hydrogenated (protiated, deuterated or tritiated) | Reduced compound |
| --- | --- |
| (Z)-1,2-diphenylethylene | 1,2-diphenylethane |
| 1,1-diphenylethylene | 1,1-diphenylethane |
| phenyl aldehyde | benzyl alcohol |
| methyl phenyl ketone | 1-phenylethanol |
| nitrobenzene | aminobenzene |
| benzene azide | aminobenzene |
| chlorobenzene | benzene |
| phenyl methyloxybenzene | phenol |

The condition where the item (4) of the invention is practiced by using a planetary ball mill may be basically the same as in the item (3) except that approximately from 0.1 to 20% of water or heavy water and approximately from 0.01 to 20% of an organic compound based on the capacity of the vessel are placed in the reaction vessel of the planetary ball mill equipment. The conversion rate of the organic compound to the hydrogenated (protiated, deuterated or tritiated) organic compound is approximately from 70 to 100% depending on the equipment used, the reaction conditions and the like.

The organic compound thus deuterated or tritiated by the item (4) of the invention is useful as a label compound used for conformation analysis and investigations of mechanisms. In the case where a drug formed of a known organic compound is deuterated or tritiated by the item (4) of the invention, there is a possibility that the medical benefit of the drug is enhanced.

The method for hydrogenating (protiating, deuterating or tritiating) an organic compound as the item (5) of the invention may be practiced in the same manner as in the item (4).

The method for dehalogenating an organic compound as the item (6) of the invention may also be practiced in the same manner as in the item (4). In particular, the method may dehalogenate an organic compound having halogen that is harmful to human bodies, such as polychlorinated biphenyl (PCB), and thus may be utilized for detoxification of the organic compound.

The items (7) to (10) of the invention may be basically the same as the items (3) to (8) except that the ball A of the item (2) is replaced by a ball for mechanochemical reaction that is essentially free of catalyst metal (which is hereinafter referred to as "a ball B"), and one or more kinds of catalyst metal selected from a transition metal selected from palladium, chromium, nickel, zinc, aluminum, magnesium, platinum, ruthenium and rhodium, and an oxide of the transition metal, and preferably a catalyst metal selected from nickel and chromium, is separately added to the reaction vessel.

In the items (7) to (10) of the invention, examples of the ball B include ones formed of such a material as zirconia, alumina, Teflon and brass. In the present invention, the expression "the ball is essentially free of catalyst metal" means that the content thereof is 0.01% or less.

In the items (7) to (10) of the invention, the catalyst metal may be added to the reaction vessel used for mechanochemical reaction in the form of powder, wire, foil or the like in an amount of 0.1 equivalent or more with respect to the substrate.

In the items (7) to (10) of the invention, the ball used for mechanochemical reaction and the catalyst are separated from each other. Accordingly, control of the reaction for forming hydrogen or heavy hydrogens, or forming a hydrogenated (protiated, deuterated or tritiated) organic compound is facilitated, and furthermore, the number of contacts of water, heavy water or an organic compound with the catalyst metal may be increased, thereby completing the reaction within a short period of time even under a low rotation number.

EXAMPLES

The present invention will be described in more detail with reference to examples below, but the invention is not limited to the examples. The planetary ball mills used in the examples have the following specifications. The acceleration generated by driving the planetary ball mill used in the examples at a certain rotation number is calculated by the following expression (1), and specifically the calculation results for the planetary ball mill used in Example 1 are shown in Table 1 below. In the following examples, the structures and the like of the products are confirmed by GC/MS and $^1$H NMR even not mentioned.

Planetary Ball Mill

Example 1

Equipment used: Planetary Ball Mill Premium Line-7, produced by Fritsch GmbH, Germany
  Rotation/revolution ratio: 1/−2
  Revolution radius: 0.07 m
  Vessel capacity: 80 mL
    material: stainless steel (SUS304)
    radius: 0.0240 m
  Composition of stainless steel (SUS304)
    Fe (approx.): 67 to 70%
    C: 0.12%
    Si: 1%
    Mn: 2%
    P: 0.06%
    S: 0.15 to 0.35%
    Cr: 17 to 19%
    Ni: 8 to 10%

Examples 3, 5 and 7 to 12

Equipment used: Planetary Ball Mill Quartet P-7, produced by Fritsch GmbH, Germany
  Rotation/revolution ratio: 1/−2
  Revolution radius: 0.067 m
  Vessel capacity: 12 mL
    material: stainless steel (SUS304)
    radius: 0.0130 m
  Composition of stainless steel (SUS304)
    Fe (approx.): 67 to 70%
    C: 0.12%
    Si: 1%
    Mn: 2%
    P: 0.06%
    S: 0.15 to 0.35%
    Cr: 17 to 19%
    Ni: 8 to 10%

$$Gn1 = \left[ rs - \left\{ rp1 \cdot \left( \frac{rp1}{rs} \cdot (1+iw)^2 \right) \right\} \right] \cdot \frac{\left( 2 \cdot \pi \cdot \frac{rpm}{60} \right)^2}{9.81} \quad \text{[Math. 1]}$$

Gn1: acceleration
rs: revolution radius
rp1: radius of vessel used
iw: rotation/revolution ratio
π: circular constant
rpm: rotation number

TABLE 1

| rpm | G |
|---|---|
| 100 | 0.78 |
| 150 | 1.76 |
| 200 | 3.12 |
| 250 | 4.88 |
| 300 | 7.03 |
| 350 | 9.56 |
| 400 | 12.49 |
| 450 | 15.81 |
| 500 | 19.52 |
| 550 | 23.62 |
| 600 | 28.11 |
| 650 | 29.14 |
| 700 | 33.80 |
| 750 | 38.80 |
| 800 | 44.15 |
| 850 | 49.84 |
| 900 | 55.88 |
| 950 | 62.26 |
| 1,000 | 68.98 |
| 1,050 | 76.05 |
| 1,100 | 83.47 |

Example 1

Investigation on Hydrogen Generation Condition

270 μL (15 mmol) of distilled water (Wako 046-16971) and 100 pieces of balls (diameter: 5 to 6 mm) formed of stainless steel (SUS304) were placed in a planetary ball mill vessel (80 mL), and the equipment was then closed and rotated for from 5 to 30 minutes at from 400 to 1,100 rpm for agitation. After completing the agitation, the gas in the vessel was collected by water displacement and analyzed for the composition thereof by GC/TCD (GC-2014, produced by Shimadzu Corporation). The obtained results are shown in Table 2.

TABLE 2

| | Rotation number (rpm) | Time (min) | Internal gas | Gas ratio (%) | | | | |
|---|---|---|---|---|---|---|---|---|
| | | | | $N_2$ | $H_2$ | $O_2$ Or Ar | $CO_2$ | CO |
| Control 1 | 0 | 0 | air | 70 | <0.1 | 21 | 0.54 | <0.1 |
| Control 2 | 0 | 0 | Ar | 5.6 | <0.1 | 80 | 0.38 | <0.1 |
| Control 3 | 0 | 0 | $H_2$ | 7.0 | 84 | 2.1 | 0.37 | <0.1 |
| Entry 1 | 1,100 | 5 | air | 78 | 13 | 6.1 | 0.6 | <0.1 |
| Entry 2 | 1,100 | 10 | air | 52 | 37 | 2.9 | 0.77 | <0.1 |
| Entry 3 | 1,100 | 20 | air | 34 | 51 | 4.5 | 0.29 | <0.1 |
| Entry 4 | 1,100 | 30 | air | 10 | 80 | 1.0 | 0.18 | <0.1 |
| Entry 5 | 800 | 30 | air | 21 | 55 | 1.4 | 0.16 | <0.1 |
| Entry 6 | 600 | 30 | air | 39 | 39 | 3.6 | 0.15 | <0.1 |
| Entry 7 | 400 | 30 | air | 76 | 13 | 2.1 | 0.25 | <0.1 |

The results show that in the processing time of 30 minutes, the amount of the gas collected is drastically increased at 600 rpm, the ratio of hydrogen in the gas is increased at 800 rpm, and the ratio of hydrogen in the gas is drastically increased at 1,100 rpm.

Example 2

Production of Palladium-Containing Ball

A hole having a diameter of 1 mm and a depth of 1 mm was formed in a ball made of stainless steel (SUS304) (diameter:

5 to 6 mm) (which may be hereinafter referred to as "a SUS ball") for use in a planetary ball mill equipment, and wire made of palladium having a diameter of 1 mm and a depth of 1 mm was embedded in the hole, thereby providing a palladium-containing ball (which may be hereinafter referred to as "a Pd ball").

Example 3

Hydrogenation Reaction of Diphenylacetylene 89.1 mg (0.50 mmol) of diphenylacetylene (1) and 270 μL (30 eq.) of distilled water were placed in a planetary ball mill vessel (12 mL), in which the palladium-containing ball produced in Example 2 and a ball made of stainless steel (SUS304) (diameter: 5 to 6 mm) were placed at the ratio shown below, and the equipment was then closed and rotated for 3 hours at 800 rpm (reversed every 30 minutes) for agitation. After a lapse of 3 hours, 10 mL of ethyl acetate was added to the ball mill vessel to provide a solution containing the reaction mixture, which was then filtered with Celite. The operation was repeated 5 times to provide a filtrate, which was then concentrated to provide a reaction product. The reaction product was confirmed by GC/MS and $^1$H NMR as a mixture containing diphenylacetylene (1), 1,2-diphenylethane (2), 1-cyclohexyl-2-phenylethane (3) and 1,2-dicyclohexylethane (4). The reaction is expressed by the following scheme.

[Chem. 1]

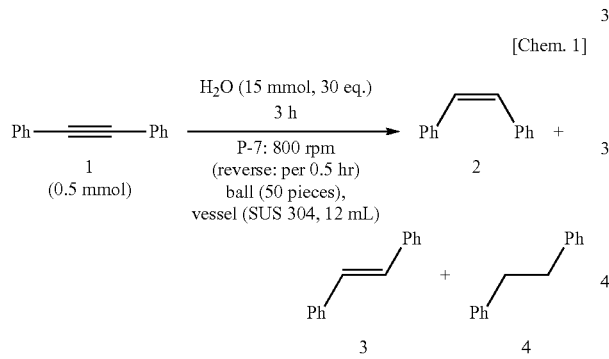

TABLE 3

|  | Pd ball | SUS ball | Ratio (1/2/3/4) |
|---|---|---|---|
| Entry 8 | 0 | 50 | 0/36/8/56 |
| Entry 9 | 1 | 49 | 2/0/1/97 |
| Entry 10 | 5 | 45 | 0/1/0/97 |
| Entry 11 | 10 | 40 | 0/6/0/94 |

The results show that the reactivity is considerably increased by at least one Pd ball, and the Pd ball is able to be used repeatedly.

Example 4

Production of Palladium-Coated Ball

A ball made of stainless steel (SUS304) (diameter: 5 to 6 mm) for use in a planetary ball mill equipment was immersed in a solution containing 158.1 mg of palladium acetate dissolved in 30 mL of methanol for one week, thereby providing a ball having a surface coated with zero-valent palladium (which may be hereinafter referred to as "a Pd-coated ball").

Example 5

Hydrogenation Reaction of 4-Chlorobenzoic Acid 78.3 mg (0.50 mmol) of 4-chlorobenzoic acid (5), 200 μL (22 eq.) of distilled water and 165 mg (2.4 eq.) of potassium carbonate were placed in a planetary ball mill vessel (12 mL), in which 50 pieces of the palladium-coated balls produced in Example 4 were placed, and the equipment was then closed and rotated for 12 hours at 800 rpm (reversed every 30 minutes) for agitation. After a lapse of 12 hours, the reaction product was processed and analyzed in the same manner as in Example 3. The reaction product was a mixture containing 4-chlorobenzoic acid (5) and benzoic acid (6). The reaction is expressed by the following scheme.

[Chem. 2]

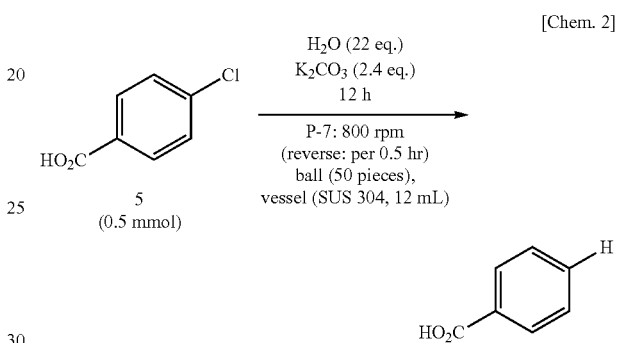

TABLE 4

|  | Kind of ball | Ratio (5/6) |
|---|---|---|
| Entry 12 | SUS Ball | 88/2 |
| Entry 13 | Pd-coated Ball | 0/91 |

The results show that the dechlorination reaction, which does not proceed substantially with the SUS ball, proceeds with a high yield with the Pd-coated ball.

Example 6

Production of Chromium-Coated Ball 50 pieces of ball made of zirconia (diameter: 5 to 6 mm) and 780 mg (15 mmol) of chromium powder were placed in a planetary ball mill vessel (12 mL), and the equipment was then closed and rotated for 3 hours at 800 rpm (reversed every 30 minutes) for agitation, thereby providing a ball having a surface coated with chromium.

Example 7

Hydrogenation Reaction of Diphenylacetylene 89.1 mg (0.50 mmol) of diphenylacetylene and 270 μL (30 eq.) of distilled water were placed in a planetary ball mill vessel (12 mL), in which 50 pieces of the chromium-coated balls (diameter: 5 to 6 mm) produced in Example 6 were placed, and the equipment was then closed and rotated for 3 hours at 800 rpm (reversed every 30 minutes) for agitation. After a lapse of 3 hours, the reaction product was processed and analyzed in the same manner as in Example 3. The reaction product was a mixture containing diphenylacetylene, 1,2-diphenylethane, 1-cyclohexyl-2-phenylethane and 1,2-dicyclohexylethane at a ratio of 14/4/20/62.

Example 8

Investigation on Catalyst Metal 89.1 mg (0.50 mmol) of diphenylacetylene (1) and 270 μL (30 eq.) of distilled water were placed in a planetary ball mill vessel (12 mL), in which 50 pieces of balls shown below (diameter: 5 to 6 mm) were placed solely or with an additive, and the equipment was then closed and rotated for 3 hours at 800 rpm (reversed every 30 minutes) for agitation. After a lapse of 3 hours, the reaction product was processed and analyzed in the same manner as in Example 3. The reaction product was a mixture containing diphenylacetylene (1), 1,2-diphenylethane (2), 1-cyclohexyl-2-phenylethane (3) and 1,2-dicyclohexylethane (4). The reaction is expressed by the following scheme.

[Chem. 3]

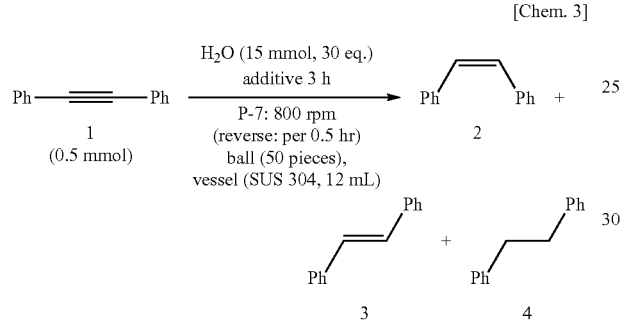

TABLE 5

|  | Ball | Additive* | Ratio (1/2/3/4) |
| --- | --- | --- | --- |
| Entry 14 | zirconia | — | No reaction |
| Entry 15 | alumina | — | No reaction |
| Entry 16 | brass | — | No reaction |
| Entry 17 | Teflon | — | No reaction |
| Entry 18 | zirconia | Ni (10 eq.) | 87/1/9/3 |
| Entry 19 | zirconia | Ni (30 eq.) | 12/15/16/58 |
| Entry 20 | zirconia | Cr (1 eq.) | 27/54/8/11 |
| Entry 21 | zirconia | Cr (3 eq.) | 0/0/0/100 |
| Entry 22 | zirconia | Cr (5 eq.) | 0/0/0/100 |
| Entry 23 | zirconia | Cr (10 eq.) | 0/0/0/100 |
| Entry 24 | zirconia | Cr (30 eq.) | 0/0/0/trace[a] |
| Entry 25 | zirconia | Fe (30 eq.) | No reaction |
| Entry 26 | zirconia | Zn (1 eq.) | 90/7/2/1 |
| Entry 27 | zirconia | Mg (1 eq.) | 10/55/8/27 |

*in the form of powder
[a]The major product was 1,2-dicyclohexylethane, which was an aromatic ring-hydrogenated product.

The results show that even in the case of using a ball made of zirconia containing no catalyst metal for mechanochemical reaction, hydrogen is formed from water, and an organic compound is hydrogenated, by adding a catalyst metal, such as nickel, chromium, magnesium, zinc or the like.

Example 9

Synthesis of 4-Aminobenzophenone Through Hydrogenation Reaction of 4-Nitrobenzophenone 91.1 mg (0.50 mmol) of 4-nitrobenzophenone (7) and 270 μL (15 mmol) of distilled water were placed in a planetary ball mill vessel (12 mL), in which 50 pieces of balls made of zirconia (diameter: 5 to 6 mm) and 78 mg (1.5 mmol) of chromium powder were placed, and the equipment was then closed and rotated for 3 hours at 800 rpm (reversed every 30 minutes) for agitation. After a lapse of 3 hours, 10 mL of ethyl acetate was added to the planetary ball mill vessel to provide a solution containing the reaction mixture, which was then filtered with Celite. The operation was repeated 5 times to provide a filtrate, which was then concentrated, and then $^1$H NMR confirmed that 4-aminobenzophenone (8) was obtained. The yield was 84%. The reaction is expressed by the following scheme.

[Chem. 4]

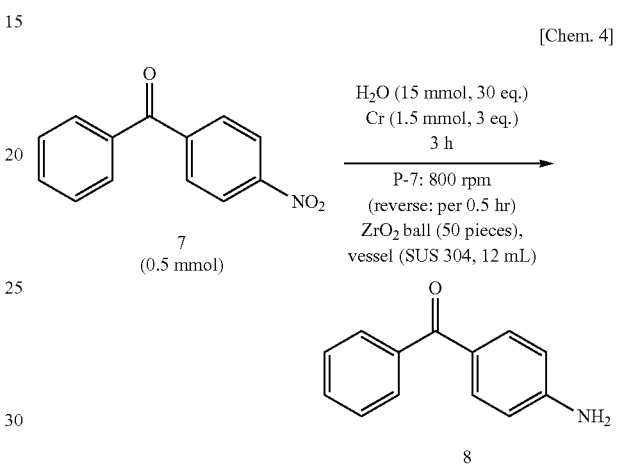

Example 10

Synthesis of 4-Amino-1-Methoxybenzene Through Hydrogenation Reaction of 1-Methoxy-4-Nitrobenzene 76.6 mg (0.50 mmol) of 1-methoxy-4-nitrobenzene (9) and 270 μL (15 mmol) of distilled water were placed in a planetary ball mill vessel (12 mL), in which 50 pieces of balls made of zirconia (diameter: 5 to 6 mm) and 78 mg (1.5 mmol) of chromium powder were placed, and the equipment was then closed and rotated for 3 hours at 800 rpm (reversed every 30 minutes) for agitation. After a lapse of 3 hours, 10 mL of ethyl acetate was added to the ball mill vessel to provide a solution containing the reaction mixture, which was then filtered with Celite. The operation was repeated 5 times to provide a filtrate, which was then concentrated, and then $^1$H NMR confirmed that 4-amino-1-methoxybenzene (10) was obtained. The yield was 17%. The reaction is expressed by the following scheme.

[Chem. 5]

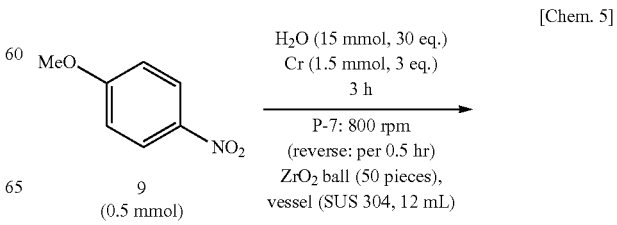

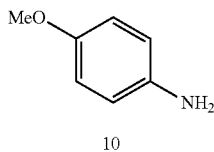

Example 11

Deuteration Reaction of Diphenylacetylene 89.1 mg (0.50 mmol) of diphenylacetylene (1) and 270 μL (30 eq.) of heavy water were placed in a planetary ball mill vessel (12 mL), in which 50 pieces of balls made of zirconia (diameter: 5 to 6 mm) and 78 mg (1.5 mmol) of chromium powder were placed, and the equipment was then closed and rotated for 3 hours at 800 rpm (reversed every 30 minutes) for agitation. After a lapse of 3 hours, 10 mL of ethyl acetate was added to the planetary ball mill vessel to provide a solution containing the reaction mixture, which was then filtered with Celite. The operation was repeated 5 times to provide a filtrate, which was then concentrated, and then $^1$H NMR confirmed that deuterated alkenes (2-$d_2$ and 3-$d_2$) and a deuterated alkane (4-$d_4$) were obtained. The yield was 61%. The reaction is expressed by the following scheme.

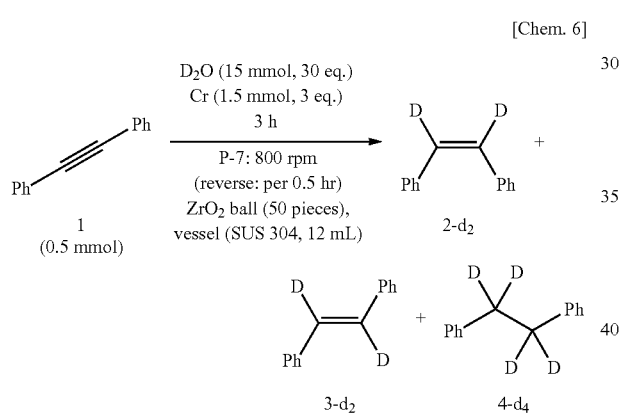

[Chem. 6]

The results show that deuteration of an organic compound is able to be performed with a ball made of zirconia containing no catalyst metal and chromium powder as a catalyst metal.

Example 12

Hydrogenation Reaction of Methyl 4-Chlorobenzoate 85.3 mg (0.50 mmol) of methyl 4-chlorobenzoate (11) and 270 μL (30 eq.) of distilled water were placed in a planetary ball mill vessel (12 mL), in which 50 pieces of balls made of zirconia (diameter: 5 to 6 mm) and 78 mg (1.5 mmol) of chromium powder were placed, and the equipment was then closed and rotated for 3 hours at 800 rpm (reversed every 30 minutes) for agitation. After a lapse of 3 hours, 10 mL of ethyl acetate was added to the planetary ball mill vessel to provide a solution containing the reaction mixture, which was then filtered with Celite. The operation was repeated 5 times to provide a filtrate, which was then concentrated, and then $^1$H NMR confirmed that methyl 4-chlorobenzoate (11) and methyl benzoate (12) were obtained. The yield was 11%. The reaction is expressed by the following scheme.

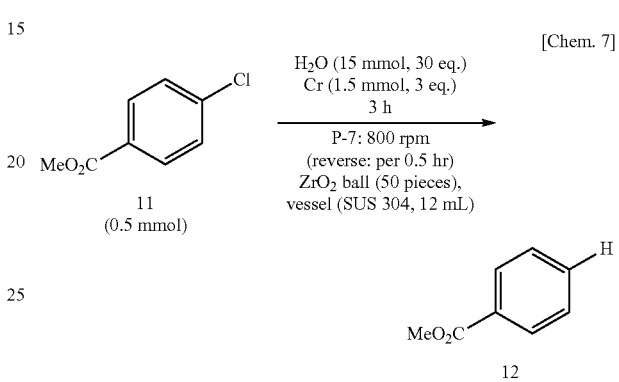

[Chem. 7]

The results show that an organic compound having halogen is able to be dehalogenated with a ball made of zirconia containing no catalyst metal and chromium powder as a catalyst metal.

INDUSTRIAL APPLICABILITY

The present invention is advantageously utilized for generation of hydrogen or heavy hydrogens, hydrogenation (protiation, deuteration or tritiation) reaction of an organic compound, and the like.

The invention claimed is:
1. A method for producing hydrogen or heavy hydrogens, the method comprising:
 subjecting water or heavy water to a mechanochemical reaction with a planetary ball mill in the presence of a catalyst metal, wherein an energy density of a rotational acceleration of 75 G or more is applied to the water or heavy water for 25 minutes or more, and a conversion rate of water or heavy water to hydrogen or heavy hydrogen is 60% or more.
2. The method according to claim 1, wherein the catalyst metal comprises a transition metal.

* * * * *